United States Patent [19]
Hwang

[11] Patent Number: 5,381,576
[45] Date of Patent: Jan. 17, 1995

[54] ELECTRICAL TOOTHBRUSH

[76] Inventor: Dong W. Hwang, 3-109 Haemaji Apartment, 1-209 Songhyun-dong, Dalsu-ku, Daegu-shi, Rep. of Korea

[21] Appl. No.: 214,199

[22] Filed: Mar. 17, 1994

[51] Int. Cl.⁶ ............................................. A61C 17/34
[52] U.S. Cl. ........................................ 15/22.1; 74/25
[58] Field of Search .................. 15/22.1, 22.2, 22.4; 74/25, 47, 82; 310/50, 80

[56] References Cited

U.S. PATENT DOCUMENTS

| | | | |
|---|---|---|---|
| 4,326,314 | 4/1982 | Moret et al. | 15/72 |
| 4,413,199 | 11/1983 | Fischer | 310/50 |

FOREIGN PATENT DOCUMENTS

| | | | |
|---|---|---|---|
| 0021651 | 2/1978 | Japan | 15/22.1 |
| 0021652 | 2/1978 | Japan | 15/22.1 |
| 59-37081 | 9/1984 | Japan . | |
| 93-4271 | 3/1993 | Japan . | |

Primary Examiner—Edward L. Roberts
Attorney, Agent, or Firm—Burns, Doane, Swecker & Mathis

[57] ABSTRACT

An electrical toothbrush according to the present invention comprising a housing, an electric motor mounted in the housing for rotating an eccentric pin, a reciprocating vibration holding shaft mounted in the upper housing for being adapted for attachment of a toothbrush thereon, the holding shaft being drivable for oscillation about its longitudinal axis, the toothbrush being interchangeably connected to the upper end of the holding shaft, transformer structure for transforming the rotary motion of the eccentric pin into a reciprocating vibratory motion of the holding shaft, the transformer comprising a cylindrical member and an elastic deformable member connected by an integral lever member.

2 Claims, 4 Drawing Sheets

ELECTRICAL TOOTHBRUSH

BACKGROUND OF THE INVENTION

This invention relates to an electrical tooth cleaning apparatus, and, more particularly, to electrical toothbrushes which oscillate smoothly and wherein the operation of electric motors is not stopped even when an user presses the toothbrush down too hard against the teeth or the gums.

FIGS. 1 and 2 show known electrical toothbrushes. FIG. 1 shows a section of a motion transformer disclosed in Japanese Publication No. 59-37081. In the disclosure, when an electric motor is running, an eccentric pin is set in a rotary motion, so that a fork driven by an eccentric pin and thereby an oscillatory toothbrush holding shaft carrying a toothbrush in a non-rotatable manner perform an oscillating movement about its longitudinal axis.

FIG. 2 shows a section of a motion transformer disclosed in U.S. Pat. No. 4,326,314, which has the same construction as that shown in Japanese Publication No. 59-37081, except that an eccentric pin extends in a freely displaceable manner through the diametrical bore of a ball of a ball joint which forms a guide member which is freely displaceable within the longitudinal slot of a fork.

In U.S. Pat. No. 4,413,199, a water-tight switch for switching an electromotor on and off is provided.

The prior art has many disadvantages. First, the direct contact of the eccentric pin with the fork during operation results in severe wear on the contact surface, thus shortening the lives of the toothbrushes. Secondly, power loss due to wear is very large. Thirdly, the long direction-turning time during oscillation results in a non-regular swing. Fourthly, when the toothbrushes are overloaded, they may be broken or the electric motor may stop. Fifthly, noise is produced during the frictional sliding movement of the eccentric pin along the fork member.

SUMMARY OF THE INVENTION

An object of the present invention is to provide an electric toothbrush having a long life, in which wear on and noise from an elastic motion transformer are prevented.

Another object of the present invention is to provide an electric toothbrush wherein an electric motor is not stopped and a reciprocating vibratory movement is maintained even when the toothbrush is overloaded.

Still another object of the present invention is to provide an electric toothbrush wherein a reciprocating vibratory movement is achieved, and injuries and bleeding of the teeth or the gums may be prevented.

An electrical toothbrush according to the present invention comprises a housing composed of an upper housing portion and a lower housing portion which are interconnected mutually; an interior space defined by the housing; an electric motor mounted in the housing for rotating an eccentric pin, the motor being connected from a battery, and switched on and off by an external switch, a reciprocating vibratory toothbrush holding shaft mounted longitudinally in the upper housing being adapted for attachment of a toothbrush thereon, the oscillatory toothbrush holding shaft being drivable for oscillation about its longitudinal axis, the toothbrush having bristles affixed to the upper end thereof and being interchangeably connected to the upper end of the oscillatory toothbrush holding shaft; means for transforming the rotary motion of the eccentric pin into a reciprocating vibratory motion of the holding shaft which carries the toothbrush, the motion transformer comprising a cylindrical member and an elastic deformable member connected by an integral lever member, the motion transformer being formed from a plastic material having toughness and flexibility; an intermediate portion having a central bore for receiving the eccentric pin and an extension to which a shorter transverse wall is connected, and a deformable film wall portion having one end connected to the integral lever member and the other end connected to the shorter transverse wall.

BRIEF DESCRIPTION OF THE DRAWINGS

The invention will be further described and illustrated with reference to the accompanying drawings, in which.

DETAILED DESCRIPTION OF THE INVENTION

Figure 1:
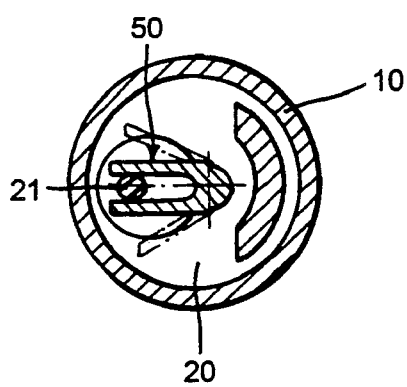
FIGS. 1 and 2 are sectional views of a motion transformer member of the prior art electric toothbrushes.
Figure 2:
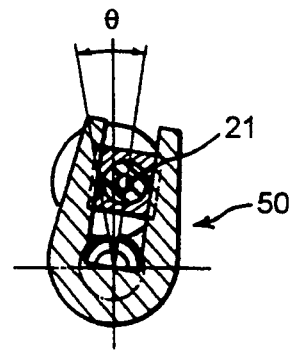

Referring to the drawings, a housing 10 constructed in the form of a handgrip and made of a plastic material comprises an upper housing portion 11 and a lower housing portion 12 which are threaded with each other, and an inner space 13. An O-ring 14 is fixedly mounted between the two housing portions 11, 12 for sealing engagement thereof.

An electric motor 20 mounted in the housing 10 is connected to batteries 23, and switched on and off by an external switch means 25 comprising a push-button 26. A wheel 22 provided with an eccentric pin 21 is mounted on the motor shaft.

Figure 7:
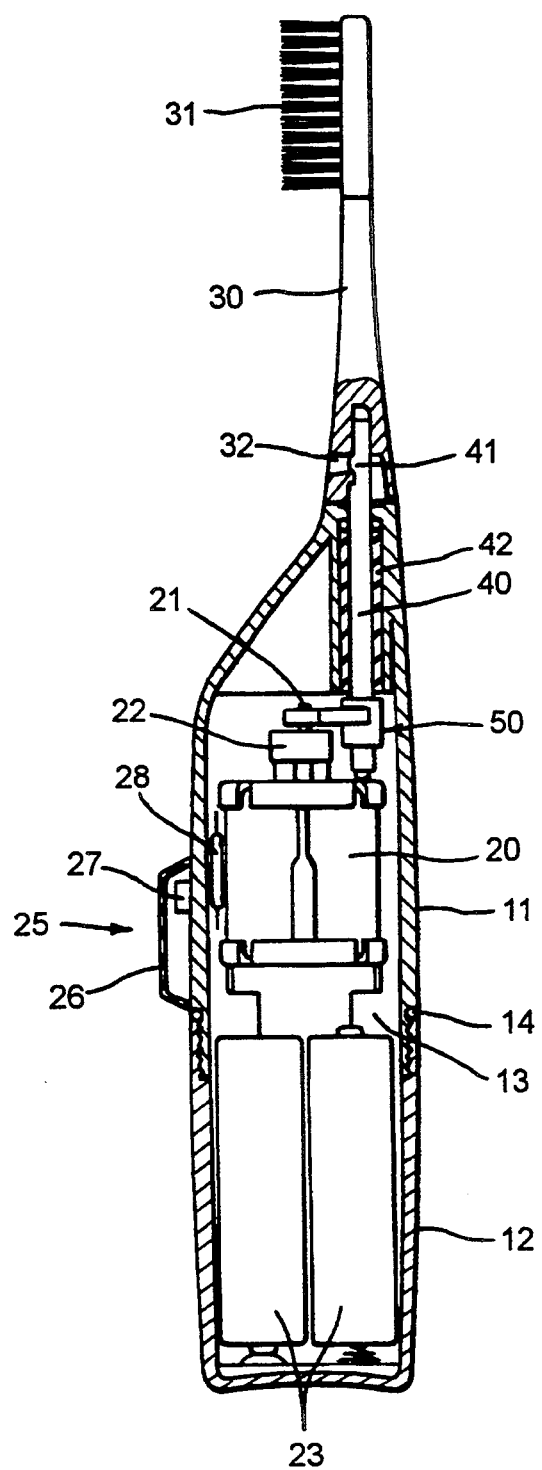
FIG. 7 is an axial section through the electric toothbrush of the present invention.
Figure 8:
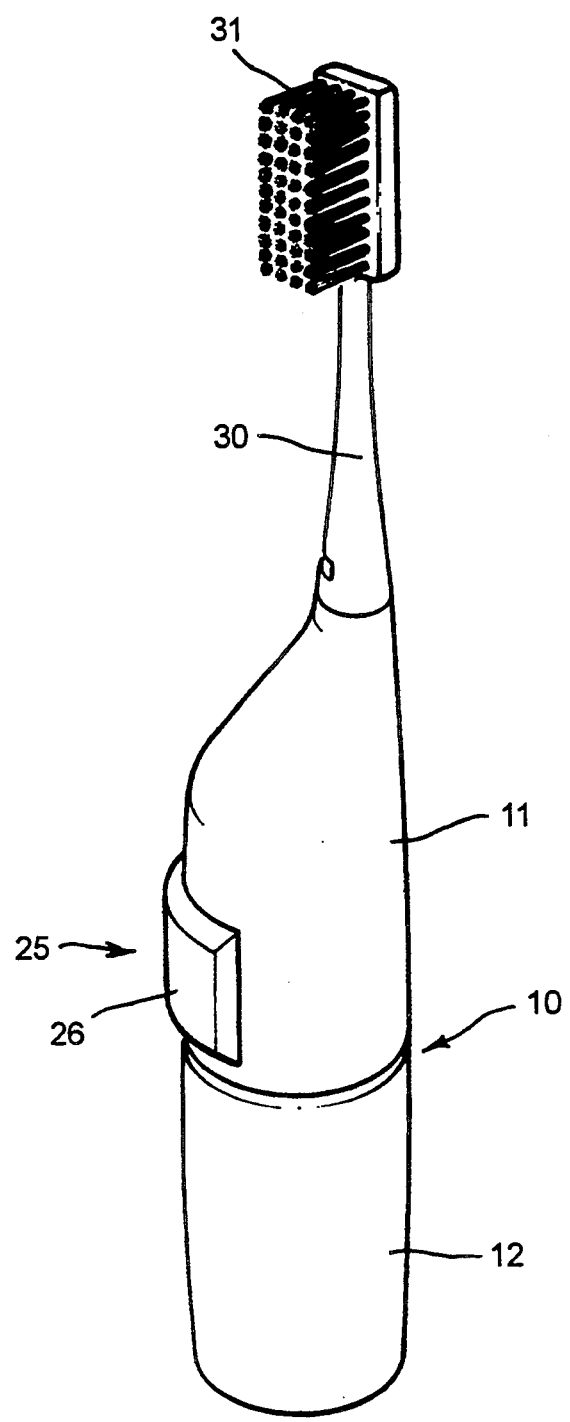
FIG. 8 is a perspective view of the electric toothbrush of the present invention.

As the switch means 25, another direct or indirect switch may be used. For example, as shown in FIG. 7, a permanent magnet 27 is fixedly mounted to the push-button 26 for moving together with the push-button 26. A reed switch 28 is mounted to the interior of the housing 10 at a portion corresponding to the movable range of the push button 26 actuated by the magnetic force produced by the permanent magnet 27. Alternatively, a resiliently mounted movable terminal which contacts with or is separated from a fixed terminal in response to the movement of the push button 26, may be used as the switch means 25 (not shown).

It is preferable to use a switch means comprising the permanent magnet 27 and the reed switch 28 in view of the fact that electrically driven toothbrushes are generally used in moist places, such as bathrooms.

An elastic deformable toothbrush 30 has bristles 31 on the upper end and slot 32 in the lower end for interchangeably attaching to an approximately semi-spherical protrusion 41 extending from the semi-cylindrical upper end of the toothbrush holding shaft 40. The holding shaft 40 is mounted in the upper housing portion 11 in a manner drivable for oscillation about its longitudinal axis in response to the rotary motion of the motor.

With this arrangement, only a slight force is enough to disassemble the toothbrush 30 from the toothbrush holding shaft 40.

Any engagement means for the toothbrush 31 and the holding shaft 40 may be used if it can assemble and disassemble the brush 31 and shaft 40 by a slight external force.

Figure 6:
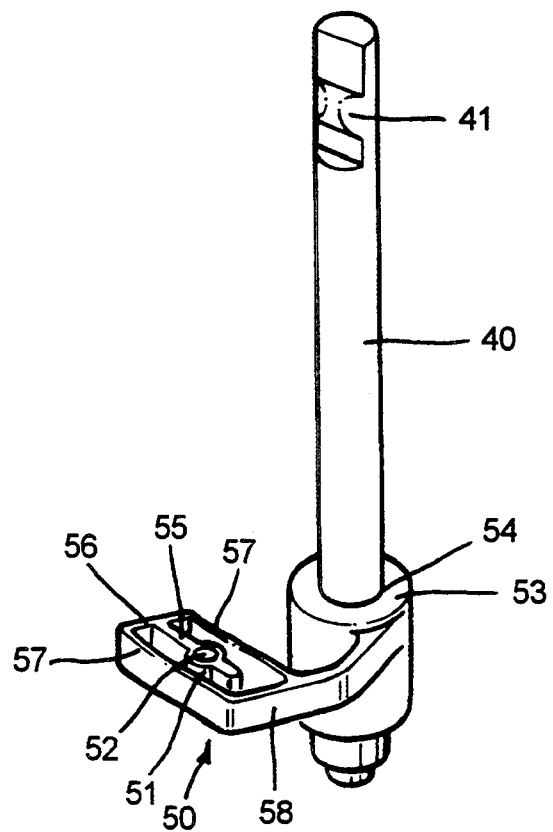
FIG. 6 is a perspective view of the assembly of the motion transformer with a reciporcating vibratory toothbrush holding shaft of the present invention.

As shown in FIG. 6, the holding shaft 40 has the lower end fixedly received in a bore 54 in a cylindrical member 53 of a motion transformer 50 for oscillatory movement about its longitudinal axis. The holding shaft 40 is retained in a bearing 42.

As shown in FIG. 7, when the motor 20 is running, the eccentric pin 21 is set in a rotary motion, so that the motion transformer 50 driven by the eccentric pin 12 and thereby the holding shaft 41 carrying the toothbrush 30 in a non-rotatable mariner perform a reciprocating vibratory movement about its longitudinal axis.

In this invention, it is important that the motion transformer 50 is made from a plastic material having toughness and flexibility such that it has durability and no noise is produced during use of the electric toothbrush of the present invention.

Referring to FIGS. 3 to 6, the motion transformer 50 has an approximately rectangular deformable member and a cylindrical member 53 which are connected by an integral lever 58. The cylindrical member 53 has a central bore 54 for fixedly receiving the lower end of the holding shaft 40.

The approximately rectangular deformable member has an intermediate portion 51 having a bore 52 in which the eccentric pin 21 is engaged. Film wall portions 57 extend generally parallel to each other. Each film wall portion 57 is connected to an integral lever 58 at one end thereof. The other end of each film wall portion 57 is connected to a transverse shorter wall portion 56 which is connected to one extension 55 of the intermediate portion 51.

The intermediate portion 51, the cylindrical member 53, the integral lever 58, the extension 55 and the film wall portions 57 are all integrally formed parts of a unitary element, for example, formed by molding from a plastic material.

As an alternative, the film wall portions 57 need not be parts of one unitary assembly but may for some purposes advantageously be formed from different components and connected to the transverse shorter wall portion 56 and the lever 58. The film wall portions 57 need not be two in number but a single film wall portion 57 may for some purposes advantageously be provided.

For preventing the tear of the film wall portions 57 at a boundary portion with the lever 58 and the transverse shorter wall 56, the boundary portions may preferably be rounded.

The operation of the electric toothbrush of the present invention is now described.

When the motor 20 is running after the push button 26 is depressed, the eccentric pin 21 is set in a rotary motion along the circle constituted by the eccentrically displaced distance from the axis of rotation of the motor 20, so that the approximately rectangular deformable member driven by the eccentric pin 21 and thereby the holding shaft 40 carrying the toothbrush 30 in a non-rotatable manner, perform a reciprocating vibratory movement about its longitudinal axis.

Figure 3:
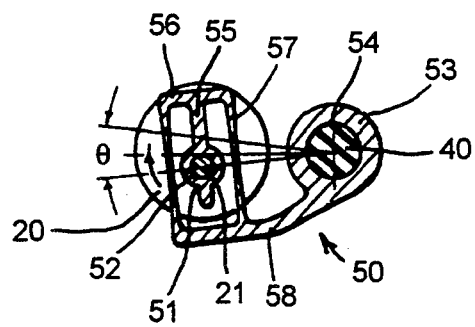
FIG. 3 is a sectional view of a motion transformer of the present invention.

FIG. 3 shows the swing angle (Θ) of the holding shaft 40 which is determined by the maximum radius the eccentric pin may have during rotation.

Figure 4A:
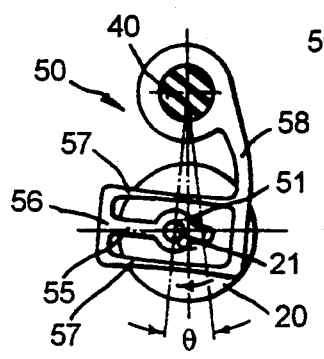
FIGS. 4-A, 4-B, 4-C and 4-D show the operation of the motion transformer of the present invention.
Figures 4B, 4C:
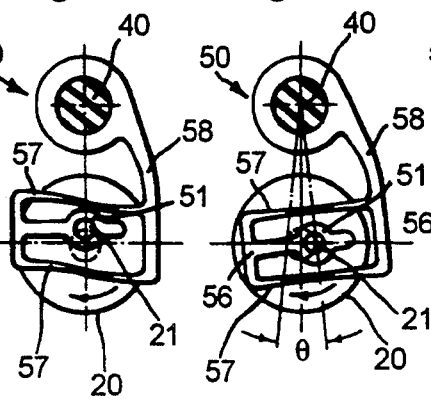
Figure 4D:
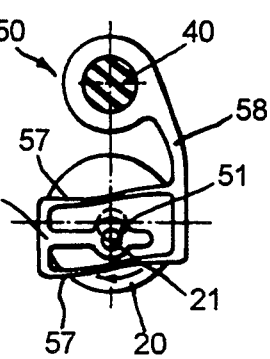

FIGS. 4-A, 4B, 4C and 4D show the position of the motion transformer in response to the location of the eccentric pin 21.

FIG. 4-A shows the eccentric pin 21 which assumes its position to the left side of the motor axis. FIG. 4-B shows the pin 21 in aligned position with the motor axis after having been rotated clockwise. In FIG. 4-B, the motion transformer 50 is further moved to the right side when compared with the pin 21 in FIG. 4-A, and the eccentric pin 21, intermediate portion 51, extension 55 and transverse shorter wall portion 56 are in their uppermost position, so that the film wall portions assume an "S" shape with the left side in the raised position.

FIG. 4-C shows the pin 21 which is continuously moved clockwise and is in its right-end position. In this position, the motion transformer 50 does not deform. FIG. 4-D shows the pin 21, intermediate portion 51, extension 55 and transverse shorter wall portion 56 in their lowermost position wherein the motion transformer 50 is further moved to the left side when compared with FIG. 4-C. Accordingly, the motion transformer 50 assumes an "S" shape with the left side in its lowered position. The cycle is repeated.

The maximum swing angle e of motion transformer 50 is determined within the rotatory radius of the pin 21.

The approximately rectangular elastic member driven by the eccentric pin 21 and thereby the holding shaft 40 carrying the toothbrush 30 in a non-rotatable manner, performs a reciprocating vibratory movement about its longitudinal axis.

With the construction, when the toothbrush is pressed down too hard, the flexible film wall portions 57 deform, thus causing the electrical toothbrush not to stop. The approximately rectangular elastic member deforms elastically depending on the degree of the load. When the load is large, the swing angle of the toothbrush 31 decreases, but the motor 20 will not stop.

Figure 5:
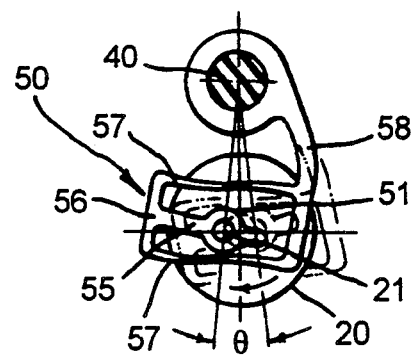
FIG. 5 is a sectional view showing the position of the motion transformer when the toothbrush is forcibly stopped.

FIG. 5 shows the condition in which the swing of the toothbrush 31 is stopped forcibly by a very large load thereon. Even in this condition, the approximately rectangular elastic deformable member is deformed, thus preventing stop of the swing of the pin 21. Accordingly, in response to the loads on the toothbrush 31, the swing angle varies. For example, when a strong force is applied to a deep place of a mouth, such as a back tooth, the swing angle of the toothbrush 30 decreases and the bristles 31 press the teeth too hard, even when the toothbrush will not stop.

What is claimed is:

1. In an electrical toothbrush having,
  a housing composed of an upper housing portion and a lower housing portion which are interconnected mutually,
  an interior space defined by the housing,
  an electric motor mounted in the housing for rotating an eccentric pin, the motor being connected from a battery, and switched on and off by an external switch,
  a reciprocating vibratory toothbrush holding shaft mounted longitudinally in the upper housing being adapted for attachment of a toothbrush thereon, the holding shaft being drivable for oscillation about its longitudinal axis, the toothbrush having bristles affixed to the upper end thereof and being interchangeably connected to the upper end of the holding shaft, means for transforming the rotary motion of the eccentric pin into a reciprocating vibratory motion of the holding shaft which carries the toothbrush, characterized in that the motion transformer comprises:

a cylindrical member and an elastic deformable member connected by an integral lever member, the motion transformer being formed from a plastic material having toughness and flexibility, an intermediate portion having a central bore for receiving the eccentric pin and an extension to which a shorter transverse wall is connected, and a deformable film wall portion having one end connected to the integral lever member and the other end connected so the shorter transverse wall.

2. An electric toothbrush according to claim 1, wherein the deformable wall portion comprises two in number formed symmetrically with respect to the extension of the intermediate portion.

* * * * *